US 10,273,353 B2

(12) United States Patent
Henry et al.

(10) Patent No.: US 10,273,353 B2
(45) Date of Patent: Apr. 30, 2019

(54) METHOD AND SYSTEM FOR PREDICTING BIOCOMPOSITE FORMULATIONS AND PROCESSING CONSIDERATIONS BASED ON PRODUCT TO BE FORMED FROM BIOCOMPOSITE MATERIAL

(71) Applicant: CNH Industrial Canada, Ltd., Saskatoon (CA)

(72) Inventors: James Henry, Saskatoon (CN); Satyanarayan Panigrahi, Saskatoon (CA); Radhey Lal Kushwaha, Saskatoon (CA)

(73) Assignee: CNH Industrial Canada, Ltd., Saskatoon, Saskatchewan (CA)

( * ) Notice: Subject to any disclaimer, the term of this patent is extended or adjusted under 35 U.S.C. 154(b) by 71 days.

(21) Appl. No.: 14/429,479

(22) PCT Filed: Jan. 30, 2015

(86) PCT No.: PCT/IB2015/000102
§ 371 (c)(1),
(2) Date: Mar. 19, 2015

(87) PCT Pub. No.: WO2015/114448
PCT Pub. Date: Aug. 6, 2015

(65) Prior Publication Data
US 2016/0017132 A1 Jan. 21, 2016

Related U.S. Application Data

(60) Provisional application No. 61/933,978, filed on Jan. 31, 2014.

(51) Int. Cl.
*G06N 3/02* (2006.01)
*C08L 23/06* (2006.01)
*G06F 19/00* (2018.01)

(52) U.S. Cl.
CPC .............. *C08L 23/06* (2013.01); *G06F 19/70* (2013.01); *G06N 3/02* (2013.01)

(58) Field of Classification Search
CPC ....................................................... G06N 3/02
(Continued)

(56) References Cited

U.S. PATENT DOCUMENTS 5,032,525 A 7/1991 Lee et al.
5,635,123 A 6/1997 Riebel et al.
(Continued)

FOREIGN PATENT DOCUMENTS

WO 2005051233 6/2005
WO 2013081812 6/2013

OTHER PUBLICATIONS

Joel-Ahmed Mubashshar Mondol ("Neural Networks Approach Towards Determining Flax—Biocomposites Composition and Processing Parameters" 2009).*
(Continued)

*Primary Examiner* — Lut Wong
(74) *Attorney, Agent, or Firm* — Rebecca L. Henkel; Rickard K. DeMille

(57) ABSTRACT

A system and method for predicting the formulation and processing method and processing parameters for the formation of a biocomposite material is provided. The system and method utilizes the desired properties for the biocomposite material and utilizes these properties m a prediction system to determine the particular formulation, processing method and processing parameters for the formation of a biocomposite material having the desired characteristics. This information is output from the prediction system to a biocomposite material manufacturing system in order to
(Continued)

form the biocomposite material and an end product formed therefrom that has the desired characteristics input into the prediction system.

17 Claims, 2 Drawing Sheets

(58) Field of Classification Search
USPC .......................................................... 706/21
See application file for complete search history.

(56) References Cited

U.S. PATENT DOCUMENTS

| 2005/0013982 | A1 | 1/2005 | Burgueno et al. |
| 2007/0260357 | A1 | 11/2007 | Issberner et al. |
| 2008/0160567 | A1 | 7/2008 | Billington et al. |

OTHER PUBLICATIONS

Tzeng et al ("A study of optimization of injection molding process parameters for SGF and PTFE reinforced PC composites using neural network and response surface methodology" 2012).*
H. K. D. H Bhadeshia ("Neural Networks in Materials Science" 1999).*
Jiang et al ("Neural network based prediction on mechanical and wear properties of short fibers reinforced polyamide composites" 2008).*
Fei et al ("Practical Applications of Taguchi Method for Optimization of Processing Parameters for Plastic Injection Moulding: A Retrospective Review" 2013).*
Allan et al., "Neural modelling of polypropylene fibre processing: Predicting the structure and properties and identifying the control parameters for specifc fibres", Journal of Materials Science, vol. 36, Issue 13, Jul. 1, 2001, pp. 3113-3118.
Tudu, P., "Processing and Characterization of Natrual Fiber Reinforced Polymer Composites", Department of Mechanical Engineering, National Institute of Technology, Rourkela-769008, 2009, 52 pages.
Patel et al., "A Review on Application of Artificial Neural Networks for Injection Moulding and Casting Processes", International Journal of Advances in Engineering Sciences, vol. 3, Issue 1, Jan. 2013, 12 pages.
Mondol et al., "Neural networks approach to biocomposites processing", 2011 IEEE Pacific Rim Conference on Communications, Computers and Signal Processing, Aug. 23, 2011, 2 pages.
Mondol et al., "Neural networks approach towards determining Flax-Biocomposites composition and processing parameters", University of Saskatchewan Electronic Theses and Dissertations, Nov. 2009, 2 pages.
Mondol et al., "Neural Networks Approach to Biocomposites Analysis", LAP Lambert Academic Publishing, Mar. 22, 2011, 3 pages.
Kadi., "Modeling the mechanical behavior of fiber-reinforced polymeric composite materials using artificial neural networks—A review", Composite Structures 73 (2006) 1-23.
Zhang et al., "Artificial neural networks applied to polymer composites: a review", Composites Science and Technolgoy 63 (2003) 2029-2044.
Tzeng et al., "A study of optimization of injection molding process parameters for SGF and PTFE reinforced PC composites using neural network and response surface methodology", The International Journal of Advanced Manufacturing Technology, Nov. 2012, vol. 63, Issue 5-8, pp. 691-704.
PCT/IB2015/000102, International Search Report and Written Opinion dated Jun. 3, 2015, 8 pages.

* cited by examiner

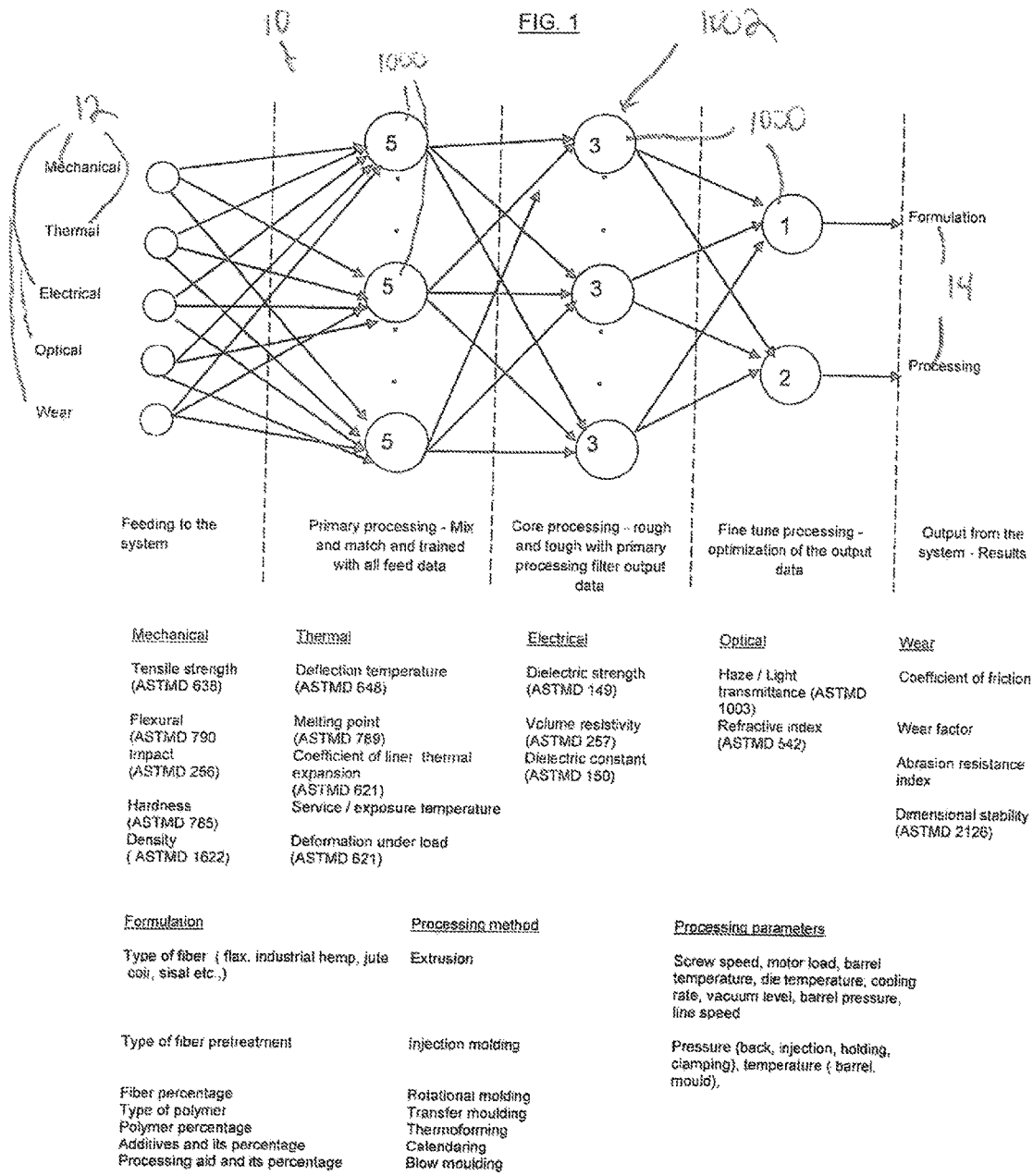

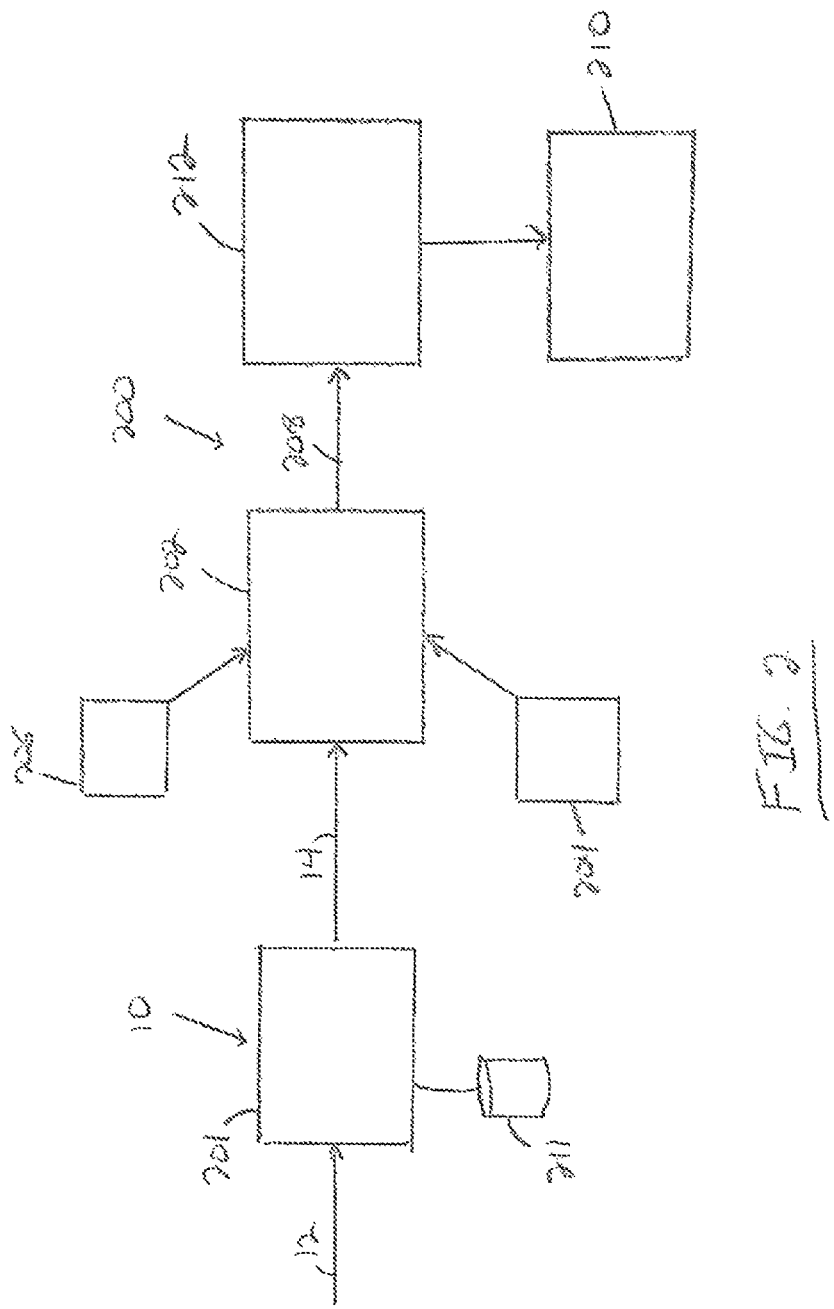

METHOD AND SYSTEM FOR PREDICTING BIOCOMPOSITE FORMULATIONS AND PROCESSING CONSIDERATIONS BASED ON PRODUCT TO BE FORMED FROM BIOCOMPOSITE MATERIAL

CROSS-REFERENCE TO RELATED APPLICATIONS

This application claims priority form U.S. Provisional Application Ser. No. 61/933,978, filed on Jan. 31, 2014, the entirety of which is expressly incorporated by reference herein.

FIELD OF THE INVENTION

The subject matter disclosed herein relates generally to biocomposite materials and, in particular, to a method and system for predicting the particular formulation processing method and associated parameters for a biocomposite material based on the desired end use for the biocomposite material.

BACKGROUND OF THE INVENTION

Biocomposites are materials formed of a combination of one or more types of fiber, one or more polymers and optionally other additives. The types and/or percentages of the various components in the biocomposite material vary in accordance with the required properties for an end product desired to be formed with the biocomposite material such that the biocomposite material can perform properly when used to form the end product.

Effective uses of biocomposites can result in cutting of material costs as the formation of biocomposites can he much more economical than the use of other materials, such as plastics, e.g., polymers, and metals. Further, the ability to vary the attributes or characteristics of the biocomposite material as desired as a result of selected variations in its composition and/or formation allows the biocomposite to be specifically tailored to enhance the quality and utility of the end product formed from the biocomposite.

While various types of biocomposites can be developed to make the desired end product, it is often difficult to particularly achieve the desired quality and properties of the product based on the proper combination of the fiber, polymer matrix, and/or the aspects of the production process used to form the biocomposite material. More specifically, in order to satisfy or meet the desired end product requirements, unless a particular biocomposite formulation has previously been developed for utilization in forming the same or a similar product, it is necessary to develop the proper biocomposite material formulation by using trial and error methods concerning at least one and likely all three variable in the manufacture of the biocomposite material, namely the fiber, polymer matrix and processing method, in addition to any additives that may need to be added to the biocomposite material. In light of the time and effort required to iteratively develop the proper biocomposite material for the product in this manner, product development utilizing biocomposite materials can often be expensive, complicated, and time intensive. However, if the biocomposite material is not optimized in this initial stage, such as by optimizing the particulars of the biocomposite formulation and processing method, then the quality of the end product formed using the resulting biocomposite material can suffer from certain defects, including a weaker and more porous end product.

As a result, in order to increase the ability to develop quality and economically viable biocomposite material products, it is desirable to provide a method for streamlining the development of the desired biocomposite material and processing method for the end product.

SUMMARY OF THE INVENTION

According to one aspect of an exemplary embodiment of the invention, a system and method is provided to predict and/or determine one or more of the variables of a biocomposite material, e.g., the formulation, processing methods and processing parameters, among others, necessary for a suitable biocomposite material composition based on the functionality performance and property requirements for the end product that is to be formed from the biocomposite material. In utilizing the method and system, manufacturers of biocomposite materials will be able to initially determine a direction or formulation starting point for the biocomposite formulation (such as, for example, the percentages of particular natural fibers, e.g., flax, hemp, jute, coir, sisal, palm, banana fiber, etc., polymer matrix, additives, chemical modification of fiber, etc.), a particular processing method or methods to be utilized to best form the product from the biocomposite material (such as extrusion, injection molding, rotational, or compression molding, among others) and what processing parameters should be used in the predetermined method or methods (sit& as the temperature, pressure, screw speed in rotations per minute, etc.) based on the required properties as measured or selected. The system and method makes these determinations for the various options for the desired biocomposite material in light of the desired properties for the end product formed of the biocomposite material, such as properties based on, but not limited to ASTM or any other equivalent standards such as ISO/BS/DIN EN, and the end use of the final product formed from the biocomposite (e.g., mechanical, thermal, optical, electrical, and wear, among others), such as those used in the agricultural, auto or construction industries, among others. it is also possible to predict the desired color and order/odor of the biocomposite by using the color/order/odor additives in the biocomposite finished product utilizing this prediction method.

These and other aspects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

The drawing furnished herewith illustrates an exemplary construction of the invention in which the above aspects, advantages and features are clearly disclosed as well as others which will be readily understood from the following description of the illustrated embodiment.

In the drawings:

FIG. 1 is a schematic illustration of a system for predicting the formulation of biocomposite formulations and processing parameters; and FIG, 2 is a schematic view of a production system for biocomposite products using the system of FIG. 1,

DETAILED DESCRIPTION OF THE INVENTION

With reference now to the drawing figures in which like reference numerals designate like parts throughout the disclosure, in FIG. 1 a system 10 and method is provided for determining the composition of a biocomposite material utilizing a step by step methodology based on experimental computation and modeling to provide the necessary information to manufacture the biocomposite. The system 10 uses mathematical tools such as finite element analysis (FEA) and/or an Artificial. Neural Network (ANN) due to its inherent structure and parallel processing capabilities, to manufacture the biocomposite by providing the desired properties of the biocomposite material as the input 12 to the system. Using these properties, the system 10 can provide an output 14 in the nature of the particular formulation and processing aspects to obtain the biocomposite having the desired properties that can be use to form an economically viable quality product. This change from the currently-used trial and error method helps in providing fast processing times and a quality end result product, along with significantly reducing wastage to enable various manufacturing industries to design and process/manufacture biocomposite materials in an economically viable and easy manner.

As stated previously, this developed system and method 10 predicts a biocomposite formulation, processing methods and processing parameters as an output 14 based on end product performance and properties requirements that are provided as an input 12 to the system. As shown in FIG. 1, the inputs 12 take the form of the desired properties for the resulting biocomposite material and product formed therefrom. These inputs 12 can cover various desired aspects, properties and/or attributes of the desired biocomposite, and in the illustrated exemplary embodiment relate to the desired mechanical, thermal, electrical, optical and wear properties of the biocomposite material to be formed. The parameters for these desired properties can be provided in any number of different types and combinations of various formats, but in the illustrated exemplary embodiment some of these parameters are provided to the system 10 in the form desired parameters for the biocomposite material, while others are provided to the system 10 in the form of hypothetical or desired test results for the biocomposite material according to certain standardized testing procedures stored within the system 10. The system 10 includes a central processing unit (CPU) or computing device 201 capable of employing the ANN and/or FEA that receives the inputs 12 regarding the desired attributes for the product 210. The CPU 201 is also connected to a database 211 in which information used by the system 10 to determine the necessary outputs 14 from the inputs 12 for producing the desired biocomposite material product 210.

For the mechanical properties provided as inputs 12, in the illustrated exemplary embodiment, some examples of the standardized testing procedure results relate to tensile strength (.ASTMD 638), flexural strength (ASTMD 790), impact strength (ASTMD 256), hardness (ASTMD 785) and density (ASTMD 1622), each of which are expressly incorporated by reference herein in their entirety. For the thermal properties provided as inputs 12, some examples of the standardized testing procedure results relate to deflection temperature (ASTMD 1648), melting point (ASTMD 789), the coefficient of linear thermal expansion (ASTMD 621), the service/exposure temperature of the end product formed from the biocomposite material, and the deformation under load (ASTMD 621), each of which are expressly incorporated by reference herein in their entirety. For the electrical properties provided as inputs 12, some examples are dielectric strength (ASTMD 149), volume resistivity (ASTMD 257) and dielectric constant (ASTMD 150), each of which are expressly incorporated by reference herein in their entirety. For the optical properties provided as inputs 12, some examples are haze/light transmittance (ASTMD 1003) and refractive index (ASTMD 542), each of which are expressly incorporated by reference herein in their entirety. Finally, for the wear properties provided as inputs 12, some examples are the coefficient of friction, the wear factor, the measure on the abrasion resistance index and dimensional stability (ASTMD 2126), which is expressly incorporated by reference herein in its entirety. Information regarding these inputs 12 can be stored in the database 211.

After determining the desired properties for the resulting biocomposite material using these standards and other measurements based upon its end use or product to be formed from the biocomposite material, the properties are provided as inputs 12 to the CPU 2.01 of the system 10 in step 100 in a conventional manner. Once entered, the CPU 201 of the system 10 performs a primary processing function step 102 in which the data concerning the properties is mixed and matched in the ANN to be utilized to arrive at a general determination of the composition and processing steps for the desired biocomposite. In step 104, a core processing step is performed in the CPU 201 in which the general determination arrived at in step 102 is further refined by primary processing and filtering the output data. Finally, in step 106, a fine tune processing step is performed by the CPU 201 of the system 10 in which the data concerning the composition and processing method for the biocomposite material is optimized in order to provide the outputs 14 from the system 10 in the form of the particular formulation and processing steps for the production of a biocomposite material having the properties specified as the inputs 12 in step 108.

In one exemplary embodiment, the system 10 utilizes the inputs 12 in a process to reverse engineer natural fiber based biocomposite, where the desired product characteristics can be provided to the system 10 as the inputs 12 and the required manufacturing information will be provided by the system 10 as output 14 for use with a specified manufacturing device and/or process.

The neural network tool/system 10 uses a number of inputs 12 to determine the particular device and/or method of production of biocomposite/biocomposite product 210. It involve a process where the desired properties of the biocomposite material and/or product 210 will be provided as inputs 12 into the neural network prediction system 10, from which the outputs 14 will provide the required formulation, processing parameters and other information to create desired biocomposite material and product 210. The neural network prediction system 10 includes experimental data and other relevant information, including but not limited to the ASTM standards discussed previously, stored in database 211 that is referred to by the system 10 and utilized, such as by extrapolation of the experimental data, in order to determine the best manufacturing devices, parameters and/or methods for the desired biocomposite material and/or product 210. The parameters or attributes that be utilized as the inputs 12 are not limited, as the system 10 can utilize any parameters that may be necessary for the system 10 to provide the outputs 14 for the formation of the material/product 210.

In one specific exemplary embodiment showing the operation of the system 10:

It was desired to find the proper formulation and processing parameters of an injection molded, flax fiber-based, high density polyethylene (HDPE) composite product with specific mechanical properties such as tensile strength, flexural strength Hardness and density for use in agricultural equipment industries.

The inputs 12 to the system 10, in addition to the injection molding, flax component and HDPE parameters were as follows:

Desired Mechanical properties of the Injection molding biocomposite:
1. Tensile strength—@ yield: 22 MPa; @break: 24 MPa
2. Flexural modulus: 900 MPa
3. Impact strength: 55 kj/m$^2$
4. Hardness: 67 D
5. Density: 1.056 g/cc$^3$ Other attributes for this product 210 provided as inputs 12 for use by the system 10 were that the material/product 210 has either an indoor or outdoor application, that moisture absorption of the material/product 210 is minimal or negligible, and that the overall processing of the material/product 210 would include a two-step process including an initial extrusion step followed by injection molding.

These inputs 12 were provided to the system 10 which was trained by using real world experimental data from database 211 with the help of Ne mal Network (NN) and selected training algorithms. Matlab® was used as the application for developing the neural network utilized in the prediction system 10. Training of the data and neurons 1000 were done in the NN system 10 to optimize the performance. Once the prediction system 10 receives the inputs 12 in the form of the data or parameters for the desired material/product 210, which in this specific example are mechanical properties, the outruns 1000 of the system 10 randomly interact with the trained data select the potential corresponding reverse order data and similar data, in the data cloud 1002 of the prediction system 10. In the system 10 each neuron 1000 takes multiple, e.g., two inputs 12 and starts a synaptic operation with neighboring relevant neurons 1000 which represents potential possible outputs 14, such as, for example formulation ingredients such as fiber weights. This operation generates the outputs 14, i.e., the selected composition of the formulation and processing parameters. in similar way other properties (spelt as thermal, electrical etc.) and/or requirements for the material/product 210 can be used as inputs 12, either individually or simultaneously with these other types of parameters to predict formulation and processing parameters for the material/product 210.

As a result of the inputs 12 provided in this example, the following prediction was provided in the form of outputs 14 from the system 10:

A. Formulation:
i. Type of fiber and % by weight: flax (25.65%-28.35%)
ii. Fiber treatment: Mercerization and silene to minimize the moisture absorption
iii. Additives % by weight: pigments (0.285%-0.315%) processing add Wax (0.0475%-0,525%), impact modifier (0.95%-1.05%), UV stabilizer (0.475%-0.525%), antistatic agent (0.095%-0,105%) oil (0.475%-0.525%,
iv. Polymers (%): HDPE 70.1%), Injection grade, MR 20.9-23.1 g/10 min B. Processing Parameters
i. Step 1: Extrusion
1. Temperature profile: 135° C.-253° C.; Die temperature 253° C.
2. Other processing parameters: Depends on type of extruder
ii. Step 2: injection molding
1. Temperature profile of barrel zone; 204° C.-221° C.
2. Pressure profile: 9.82-10.86 MPa injection pressure to fill up the mold without causing shrinkage or flash, short-shots, voids, pinholes, burns etc.

Other processing parameters, such as the pressure profile, depends on the type of injection molding machine, part size, and material specification such as MFI etc., which can additionally be utilized as inputs 12 to the system 10 depending on the level of specificity desired from the system 10.

In an exemplary embodiment of the system 10, the system 10 provides outputs 14 as guidelines with a range of ±5% error for the formulation and processing parameters. In addition, this range can be increased to ±10% if necessary to accommodate other considerations regarding the production and parameters of the biocomposite material. It helps to the processor to adjust formulation and processing parameters according ingredients quality, processing machines and mold.

While the outputs 14 can be provided by the system 10 in any number of Various types and formats, in the illustrated exemplary embodiment sonic examples of these outputs 14 are, for the composition of the biocomposite material output 14, the type(s) of fiber to be used (flax, sisal, industrial hemp, and jute, among others), the type of any fiber pretreatment to be used the fiber(s) percentage(s), the types of polymer to be utilized, the polymer(s) percentage(s), the additives to be used and their percentages, and any processing aids to be used and their percentages. For the method component of the processing output 14, some examples of this output 14 include whether the process utilizes extrusion, injection molding, transfer molding, thermoforming, calendaring or blow molding, among others. The parameter component of the processing output 14 includes, but are not limited to, the screw speed, motor load, barrel temperature, die and/or mold temperature, cooling rate, vacuum level band pressure, line speed, and pressure (hack, injection, holding and or clamping).

In one exemplary embodiment of the system 10, an artificial neural network (ANN) tool 201 is used for biocomposite processing and to develop the ANN system 10, Experimental mechanical data was collected for flax based biocomposite materials by using extruder and injection molding process and was utilized as baseline information to train the system 10. At this stage, the ANN system 10 was developed based on the mechanical properties (e.g. tensile strength, impact strength etc.) to he provided as inputs 12 and Was able to predict the formulation and processing parameters which were provided as outputs 14. Based on this development of the system 10, combination of other properties (i.e., thermal, electrical, optical etc) and other processing methods (e.g., Rotational molding) and parameters, experimental data can be utilized to train the ANN system 10 to predict biocomposite formulation and processing parameters for product development. FEA (Finite Element Analysis) can be used to develop a system 10 capable of a similar prediction for biocomposite.

Looking now at FIG. 2, in an exemplary embodiment of the invention, the system 10 is incorporated into a biocomposite production or manufacturing system 200. The inputs 12 to the system 10 enable the system 10 to determine the outputs 14 that are transmitted from the ANN and/or FEA on the CPU 201 or other similar computing device forming a part of the system 10 to the manufacturing system 200. The outputs 14 arc received in the system 200 and are utilized to select the required fiber material(s) 204 and the amounts and/or percentages thereof, and any optional additives 206 into a compounder 202 to mix the fiber(s) 204 and additives 206 in the manner identified by the system 10 via the outputs 14. From the compounder 202 the mixed material 208 is directed to a forming or molding device 212. The molding device 212 can be any suitable type of molding device and its particular type is determined based upon the information provided in the outputs 14 from the system 10. The type and operational parameters of the molding device 212 are determined by the outputs 14 from the system 10 in order to form the biocomposite material product 210.

It should he understood that the invention is not limited in its application to the details of construction and arrangements of the components set forth herein. For example, with the system and method of the present disclosure, it is also possible to predict the desired color and order of the biocomposite by using the color/order additives in biocomposite finished product. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the hest modes known for practicing the invention and will enable others skilled in the art to utilize the invention.

We claim:

1. A method for predicting the composition, processing method and processing parameters for formation of a biocomposite material having desired properties, the method comprising the steps of:
   providing inputs to a prediction system in the form of the desired properties for the biocomposite material;
   processing the inputs in view of data stored in the prediction system;
   providing outputs from the prediction system in the form of one or more of a formulation for the biocomposite material, a processing method for formation of the biocomposite material and processing parameters for the processing method for formation of the biocomposite material;
   employing the outputs in a biocomposite manufacturing system to form a biocomposite material, wherein the processing parameter outputs consist of: a molding process, screw speed, motor load, barrel temperature, die and/or mold temperature, cooling rate, vacuum level, barrel pressure, line speed, back pressure, injection pressure, holding pressure, and combinations thereof.

2. The method of claim 1 wherein molding process output is selected from the group consisting of extrusion, injection molding, transfer molding, thermoforming, calendaring and blow molding of the biocomposite material to form the end product.

3. The method of claim 1 wherein the desired properties are properties relating to the biocomposite material or an end product formed from the biocomposite material.

4. The method of claim 3 wherein the desired properties are selected from the group consisting of tensile strength, flexural strength, impact strength, hardness and density of the biocomposite material, and combinations thereof.

5. The method of claim 3 wherein the desired properties are selected from the group consisting of deflection temperature, melting point, the coefficient of linear thermal expansion, the service/exposure temperature of an end product formed from the biocomposite material, and the deformation under load of the biocomposite material, and combinations thereof.

6. The method of claim 3 wherein the desired properties are selected from the group consisting of dielectric strength, volume resistivity and dielectric constant of the biocomposite material, and combinations thereof.

7. The method of claim 3 wherein the desired properties are selected from the group consisting of haze/light transmittance and refractive index of the biocomposite material, and combinations thereof.

8. The method of claim 3 wherein the desired properties are selected from group consisting of the coefficient of friction, the wear factor, the measure on the abrasion resistance index and dimensional stability of the biocomposite material, and combinations thereof.

9. The method of claim 1 wherein tie step of providing outputs from the prediction system comprises sending the outputs from the prediction system to a biocomposite manufacturing system for forming an end product from the biocomposite material.

10. The method of claim 9 wherein the step of sending outputs from the prediction system to the manufacturing system comprises sending providing outputs on the molding method for forming the biocomposite material into the end product.

11. The method of claim 9 wherein the step of sending outputs from the prediction system to the manufacturing system comprises sending outputs on the processing parameters for the method for forming the biocomposite material into the end product.

12. The method of claim 9 where in the step of sending outputs from the prediction system to the manufacturing system comprises sending outputs on the fiber material to be used for forming the biocomposite material.

13. The method of claim 12 wherein outputs on the fiber material are selected from the group consisting of the type(s) of fiber to be used, the type of any fiber pretreatment to be used, the fiber(s) percentage(s), the types of polymer to be utilized, the polymer(s) percentage(s), the additives to he used and their percentages, and any processing aids to be used and their percentages, and combinations thereof.

14. The method of claim 1 further comprising the step of employing the outputs in a biocomposite manufacturing system to form an end product from the biocomposite material after forming the biocomposite material.

15. A system for forming an end product of a biocomposite material, the system comprising:
    a prediction system configured to
       receive inputs in the form of the desired properties for the biocomposite material;
       process the inputs in view of data stored in the prediction system; and
       provide outputs in the form of one or more of a formulation for the biocomposite material, a processing method for formation of the biocomposite material and processing parameters for the processing method for formation of the biocomposite material, and;

a biocomposite material manufacturing system configured to receive the outputs from the prediction system and to manufacture a biocomposite material and/or biocomposite material end product using the outputs on the material formulations and the processing parameters employing the outputs in a biocomposite manufacturing system to thrill a biocomposite material, wherein the processing parameter outputs consist of: a molding process, screw speed, motor load, barrel temperature, die and/or mold temperature, cooling rate, vacuum level, barrel pressure, line speed, back pressure, injection pressure, holding pressure, and combinations thereof.

16. The system of claim 15 wherein the prediction system includes a central processing unit that employs mathematical tools selected from the group consisting of finite element analysis (FEA) and/or an Artificial Neural Network (ANN), and combinations thereof.

17. The system of claim 15 wherein the biocomposite material manufacturing system comprises at least one molding device that is operated in response to the output from the prediction system.

* * * * *